US010328138B2

(12) United States Patent
McClean et al.

(10) Patent No.: US 10,328,138 B2
(45) Date of Patent: Jun. 25, 2019

(54) **VACCINE FOR TREATMENT OR PREVENTION OF *BURKHOLDERIA* INFECTION IN A MAMMAL**

(71) Applicant: INSTITUTE OF TECHNOLOGY, TALLAGHT, Dublin (IE)

(72) Inventors: Siobhan McClean, Dublin (IE); Minu Shinoy, Dublin (IE)

(*) Notice: Subject to any disclaimer, the term of this patent is extended or adjusted under 35 U.S.C. 154(b) by 0 days.

(21) Appl. No.: 14/653,826

(22) PCT Filed: Dec. 18, 2013

(86) PCT No.: PCT/EP2013/077192
§ 371 (c)(1),
(2) Date: Jun. 18, 2015

(87) PCT Pub. No.: WO2014/096070
PCT Pub. Date: Jun. 26, 2014

(65) Prior Publication Data
US 2015/0343044 A1    Dec. 3, 2015

(30) Foreign Application Priority Data

Dec. 18, 2012   (EP) .................................... 12197902

(51) Int. Cl.
*A61K 39/02* (2006.01)
*A61K 45/06* (2006.01)
*C07K 16/12* (2006.01)
*A61K 39/104* (2006.01)
*A61K 39/00* (2006.01)

(52) U.S. Cl.
CPC ............ *A61K 39/02* (2013.01); *A61K 39/104* (2013.01); *A61K 45/06* (2013.01); *C07K 16/1203* (2013.01); *A61K 2039/53* (2013.01); *A61K 2039/55505* (2013.01)

(58) Field of Classification Search
None
See application file for complete search history.

(56) References Cited

FOREIGN PATENT DOCUMENTS

| WO | 2008/017826 A2 | 2/2008 | |
|---|---|---|---|
| WO | 2008/039838 A2 | 4/2008 | |
| WO | 2011/125015 A2 | 10/2011 | |
| WO | WO 2011125015 A2 * | 10/2011 | ......... A61K 7/48338 |
| WO | WO-2012097185 A2 * | 7/2012 | ........... A61K 39/104 |
| WO | WO 2013039857 A1 * | 3/2013 | ............. C07H 21/02 |

OTHER PUBLICATIONS

McClean et al. 2009 (*Burkholderia cepacia* complex: epithelial cell pathogen confrontations and potential for therapeutic intervention; Journal of Medical Microbiology 58:1-12).*
Guo et al. 2004 ("Protein tolerance to random amino acid change", Proceedings of the National Academy of Sciences USA, vol. 101, No. 5, pp. 9205-9210, 2004).*
Greenspan et al. 1999 (Defining epitopes: It's not as easy as it seems; Nature Biotechnology, 17:936-937).*
Gauthier et al. 2000 (Protease production by *Burkholderia pseudomallei* and virulence in mice; Acta Tropica 74: 215-220).*

* cited by examiner

*Primary Examiner* — Mary Maille Lyons
(74) *Attorney, Agent, or Firm* — Cotman IP Law Group, PLC

(57) ABSTRACT

An agent for use in a vaccine therapy to prevent or treat a *Burkholderia* infection in a mammal, wherein the agent is selected from a polypeptide of SEQUENCE ID NO:1, or a therapeutically effective variant thereof having at least 90% sequence identity with SEQUENCE ID NO: 1; a polypeptide of SEQUENCE ID NO:3, or a therapeutically effective variant thereof having at least 90% sequence identity with SEQUENCE ID NO: 3; and an immunogenic portion of the polypeptides of SEQUENCE ID NO:1 or SEQUENCE ID NO:3.

4 Claims, 7 Drawing Sheets

Specification includes a Sequence Listing.

FIG. 1A

```
mnnlhrelap  issaaweqie  eevartfkrs  vagrrvvdve  gpkgpelsav
gtghlrdvaa  prehvdarlr  evrtiveltv  pfeldraaid  svergardad
wqaakeaaqr  lafaedsaif  dgypaagivg  iregtsnrkl  tlpsdvgayp
daisdaleal  rlagvdgpys  vllgadayta  lseardqgyp  viehikrivs
geiiwapais  ggcvlstrgg  dyelhlgedv  sigyashtdk  vvrlylretl
tflmltseas  vavapaagtp  a
```

FIG. 1B

```
ATGAACAATCTGCACCGCGAACTCGCGCCGATCTCCAGCGCCGCCTGGGAGCAAATCGAGGAAGAAGTCG
CGCGCACCTTCAAGCGGTCGGTGGCCGGCCGCCGCGTGGTCGACGTCGAGGGCCCGAAGGGCCCCGAACT
CTCGGCCGTCGGCACCGGGCACCTGCGCGACGTCGCGGCGCCGCGCGAGCACGTCGATGCGCGGCTGCGC
GAGGTGCGCACGATCGTCGAGCTGACGGTGCCGTTCGAACTCGACCGCGCGGCGATCGACAGCGTCGAGC
GCGGCGCGCGCGACGCCGACTGGCAGGCGGCCAAGGAAGCCGCGCAGCGACTCGCGTTCGCGGAAGACAG
CGCGATCTTCGACGGCTATCCGGCCGCCGGCATCGTCGGGATCCGCGAAGGCACGTCGAACCGCAAGCTC
ACGCTGCCGAGCGACGTCGGCGCCTATCCGGACGCCATCAGCGATGCGCTCGAGGCGCTGCGCCTCGCGG
GCGTCGACGGCCCGTACTCGGTGCTGCTCGGCGCCGACGCCTATACCGCGCTCAGCGAGGCACGCGATCA
GGGCTATCCGGTCATCGAGCACATCAAGCGGATCGTCAGCGGCGAGATCATCTGGGCGCCGGCGATCAGC
GGCGGCTGCGTGCTGTCGACGCGCGGCGGCGATTACGAGCTTCATCTCGGCGAAGACGTGTCGATCGGCT
ATGCGAGCCACACCGACAAGGTCGTTCGCCTGTATCTGCGCGAAACCTTGACGTTCCTGATGCTGACGAG
CGAAGCGTCGGTCGCGGTCGCGCCGGCCGCCGGCACGCCCGCCTGATGCGCCGCCGCGCGTGATGCCGG
```

FIG. 2A

```
mhqtndtirt  riiaaavvaa  svalpslaqa  aspgdgihqg  dvlvrlrais
iqpnergsdt  lgalnvgvnn  aivpeldfty  mirdylgvel  ilgtsrhqvt
ssaghlggvn  vlpptlllqy  hfnhagkvrp  yvgaglnyty  fynnglnvgg
egvsigkssf  gpalqfgvdv  qmtkrvflnv  dvkkiwmstd  atlgdrgigt
lhidplivgv  gvgmk
```

FIG. 2B

```
ATGCATCAAACCAATGACACGATTCGAACACGCATCATCGCCGCGGCCGTGGTGGCCGCGAGCGTCGCGC
TGCCGTCGCTCGCGCAGGCGGCGTCGCCCGGCGACGGCATTCATCAGGGCGACGTGCTCGTGCGGCTGCG
CGCGATCAGCATCCAGCCGAACGAGCGCGGCAGCGACACGCTCGGCGCGCTGAACGTCGGCGTGAACAAC
GCGATCGTGCCGGAGCTCGACTTCACGTACATGATCCGCGACTACCTGGGCGTCGAGCTGATCCTCGGCA
CGTCGCGGCATCAGGTGACGTCGAGCGCGGGCCATCTCGGCGGCGTGAACGTGCTGCCGCCGACGCTGCT
GCTGCAGTACCACTTCAATCATGCGGGCAAGGTGCGGCCGTACGTCGGCGCGGGGCTGAACTACACGTAC
TTCTACAACAACGGGCTCAACGTCGGCGGCGAGGGCGTGTCGATCGGCAAGAGCAGCTTCGGGCCGGCGC
TGCAGTTCGGCGTGGACGTGCAGATGACGAAGCGCGTGTTCCTGAACGTCGACGTGAAGAAGATCTGGAT
GAGCACGGACGCGACGCTCGGCGACCGCGGCATCGGCACGCTGCATATCGATCCGCTGATCGTCGGCGTG
GGTGTCGGGATGAAGTTCTAG
```

FIG. 3
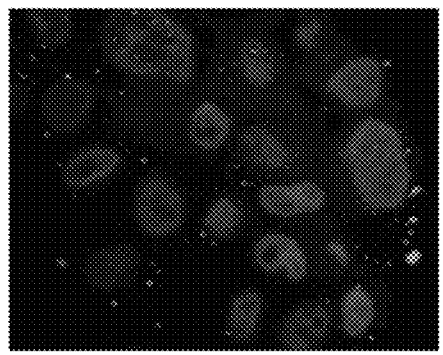
A
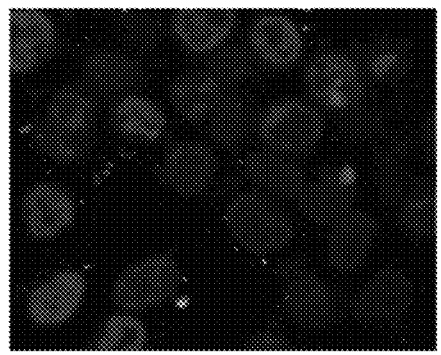
B
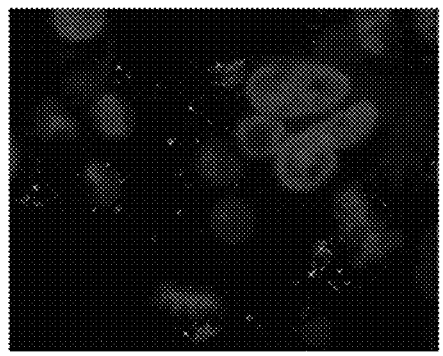
C
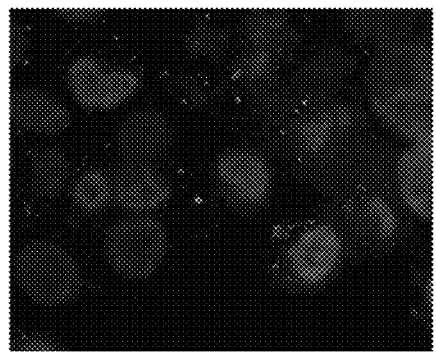
D

FIG. 4
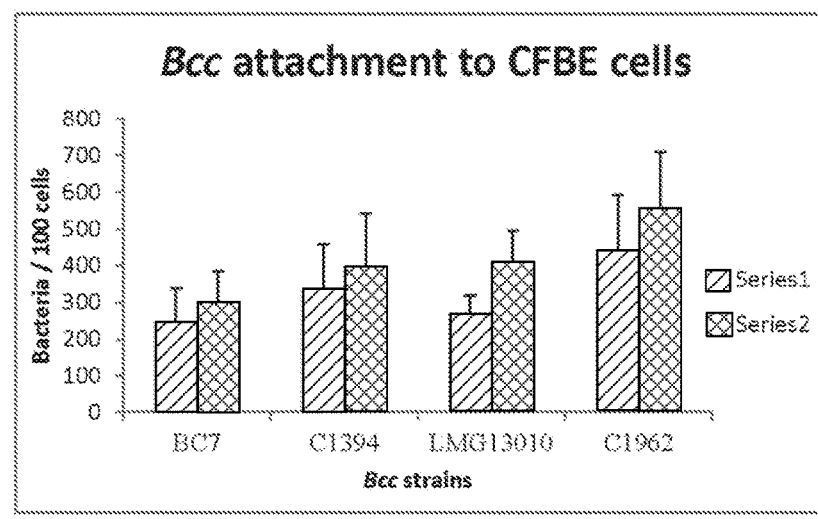
A
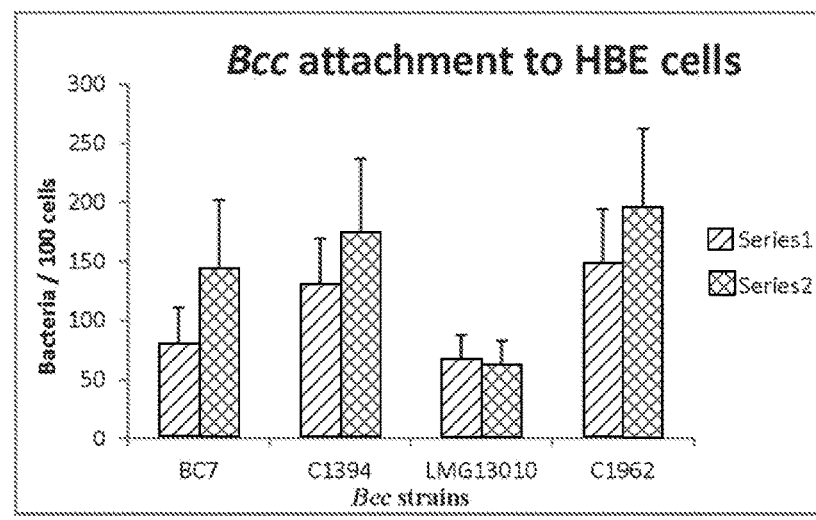
B

FIG. 5
A
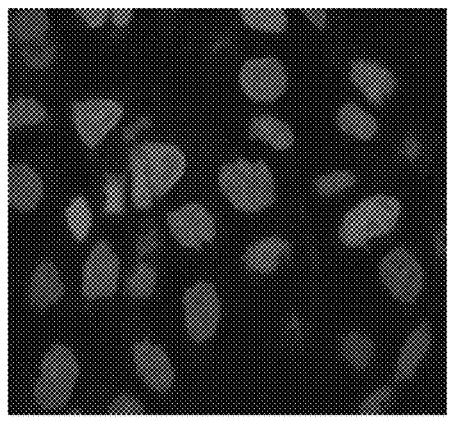
B
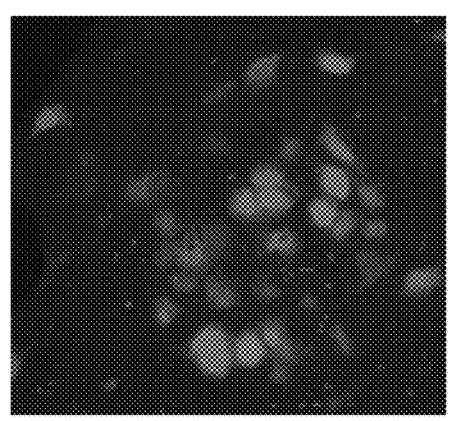
C
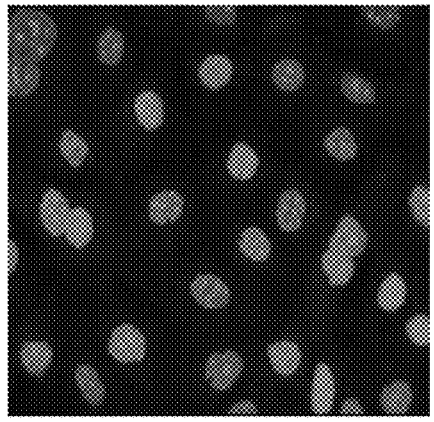
D
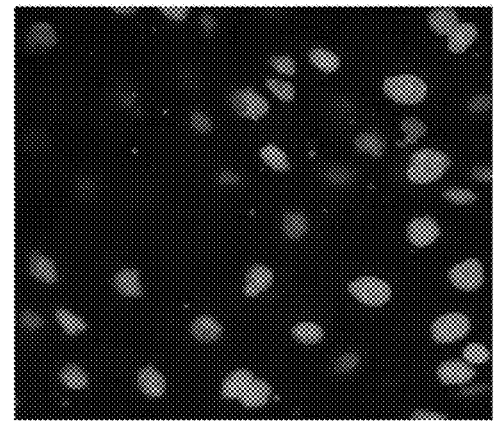

VACCINE FOR TREATMENT OR PREVENTION OF *BURKHOLDERIA* INFECTION IN A MAMMAL

TECHNICAL FIELD

The invention relates to a vaccine for treatment or prevention of *Burkholderia* infection in a mammal. In particular, the invention relates to a vaccine for treatment or prevention of chronic lung infection by *Burkholderia cepacia* complex (Bcc) in a patient with cystic fibrosis (CF).

BACKGROUND TO THE INVENTION

*Burkholderia cepacia* complex (Bcc) is a group of 17 species of Gram negative bacteria [1-3], two of which, *B. multivorans* and *B. cenocepacia*, are particularly virulent [4]. Bcc is reported to cause infections in 3.5% of CF patients in the world, which is significant, as CF patients colonised with Bcc experience a more rapid decline than those colonised with the more commonly acquired pathogen, *P. aeruginosa* [5]. Once a patient is colonised with Bcc, it is rarely eradicated due to the resistance of Bcc to antibiotics [6] and its inherent resistance to antimicrobial peptides [7, 8]. Strict segregation measures have limited patient-to-patient spread [9] and the majority of acquisitions are from the environment with *B. multivorans* being most frequently acquired; therefore Bcc still represents a substantial threat to CF patients. Furthermore, Bcc contamination of pharmaceutical formulations, medical devices and disinfectants has led to number of recent outbreaks among both CF and non-CF populations. [3, 10]. Furthermore, Bcc is an emerging pathogen in nosocomial infections among chemotherapy patients and other immunosuppressed individuals [11, 12].

Bcc is unique among CF pathogens in that it invades the lung epithelium and escapes beyond the lung. Previous work by the Applicant has shown that Bcc attaches laterally to the surfaces of epithelial cells, prior to invasion inside the cells [13].

There have been only two in vivo mouse vaccination studies reported against Bcc, both of which involved unpurified OMP preparations. Bertot et al. described the protection of mice against either *B. cenocepacia* or *B. multivorans* challenge following nasal immunisation of mice with an enriched OMP preparation administered with the mucosal adjuvant adamantylamide dipeptide [14]. More recently mice were protected from *B. cenocepacia* using enriched OMPs which were administered intranasally as a nanoemulsion preparation [15]. Both studies demonstrate the potential for OMPs as protective antigens, but were carried out with unpurified OMP preparations, which are ill-defined, rather than pure specific identified specific antigens. A 17 kDa OMP was identified as an immunodominant antigen in the latter study [15].

In addition, two related organisms, *Burkholderia pseudomallei* and *Burkholderia mallei* are also members of this genus. *Burkholderia pseudomallei*, the causative agent of melioidosis, is a Gram-negative, intracellular pathogen endemic in Southeast Asia and Northern Australia. The disease is considerably variable in humans ranging from acute septicaemia, pneumonia to chronic or latent infection which can persist and emerge decades later. It has recently been identified in the CF and CGD population also. The bacterium is intrinsically antibiotic resistant and has a mortality rate up to 50%; however despite its significant morbidity and mortality, there is currently no licensed vaccine against this infection. *B. mallei* is an obligate pathogen which causes glanders in horses. It is highly infectious in humans by aerosol route there have been concerns it may be used as means of biological warfare. No effective vaccines or therapeutics of either melioidosis or glanders currently exist It is an object of the invention to overcome at least one of the above-referenced problems.

STATEMENTS OF INVENTION

Broadly, the invention is based on the discovery of two proteins that are expressed on the membrane of pathogenic *Burkholderia* strains. The proteins are a 29 kDa membrane protein (hereafter termed "Linocin") and a 22 kDa membrane protein (hereafter termed "OMPW" or "OmpW"). Both proteins are expressed by clinically relevant strains of *B. cenocepacia* and *B. multivorans*, which constitute the most virulent strains of the *Burkholderia cepacia* complex (Bcc). The Applicant presents data showing that both membrane proteins are involved in lung cell attachment (FIG. 5), that CF patients colonised with Bcc have antibodies to Linocin and OMPW in their serum, and that mice immunised with Linocin or OMPW were protected from subsequent challenge by *B. cenocepacia* and *B. multivorans* (FIGS. 6 and 7). Thus, the invention provides two proteins, each of which provides protective immunity against the two most prevalent causative agents for Bcc infection, *B. cenocepacia* and *B. multivorans*. The Applicant has also discovered that *B. pseudomallei* and *B. mallei* both express OmpW family proteins (GI: 134251653) and GI:53723545, respectively) which are up to 89% identical (Blastp) to the *B. multivorans* OMPW protein described below. *B. mallei* and *B. pseudomallei* are 99% identical at the nucleotide level.

Accordingly, in a first aspect, the invention relates to Linocin and/or OMPW, or an immunogenic portion of either protein, or a combination of an immunogenic portion from each protein, for use in a vaccine therapy to prevent infection by a *Burkholderia* pathogen in a patient, for example infection by one or more of *B. cenocepacia, B. multivorans, B. pseudomallei* and *B. mallei*. In a preferred embodiment, the *Burkholderia* pathogen comprises Bcc. Suitably, the infection is a chronic lung infection in a patient, and suitably chronic lung infection in an immunocompromised patient, such as a patient with cystic fibrosis (CF) or chronic granulomatous disease.

The invention relates to Linocin and/or OMPW, or an immunogenic portion of either protein, or a combination of an immunogenic portion from each protein, for use in a vaccine therapy to prevent chronic lung infection by Bcc in an immunocompromised patient, such as a patient with cystic fibrosis (CF) or Chronic granulomatous disease.

The invention relates to OMPW, or an immunogenic portion thereof, for use in a vaccine therapy to prevent infection in a mammal by *B. pseudomallei* and *B. mallei*. The invention relates to OMPW, or an immunogenic portion thereof, for use in a vaccine therapy to prevent melioidosis in a mammal, especially a human. The invention relates to OMPW, or an immunogenic portion thereof, for use in a vaccine therapy to prevent glanders in a mammal, especially an equine mammal such as a horse.

The invention also relates to Linocin and/or OMPW, or an immunogenic portion of either protein, or a combination of an immunogenic portion from each protein, for use in a therapy to induce an immune response against a *Burkholderia* infection in a patient, suitably Bcc infection. Typically the patient has a chronic lung infection, and suitably is an immunocompromised patient such as a patient with cystic fibrosis patient or chronic granulomatous disease.

The invention also relates to an immunogenic composition comprising Linocin and/or OMPW, or a combination of an immunogenic portion from each protein, and optionally an adjuvant. The composition may also include one or more additional antigens.

The invention also relates to a vaccine comprising Linocin or OMPW, or a combination of an immunogenic portion from each protein, and optionally an adjuvant. The vaccine may also include one or more additional antigens.

The invention also relates to a pharmaceutical composition comprising Linocin and/or OMPW, or a combination of an immunogenic portion from each protein, and a pharmaceutically acceptable excipient. The composition may also include one or more additional antigens.

The invention also relates to a substantially pure protein selected from Linocin or OMPW.

The invention also relates to an isolated anti-Linocin or anti-OMPW antibody.

The invention also relates to a method of treating or preventing a *Burkholderia* infection, in a patient, comprising a step of administering to the patient a therapeutically effective amount of Linocin and/or OMPW, or a combination of an immunogenic portion from each protein. Typically, the Linocin, OMPW, or immunogenic portion thereof, is administered to the patient by pulmonary or intranasal administration.

The invention also relates to a method of treating or preventing Bcc infection in a patient, typically a patient with a chronic lung infection, suitably an immunocompromised patient such as a patient with cystic fibrosis or chronic granulomatous disease, comprising a step of administering to the patient a therapeutically effective amount of Linocin and/or OMPW, or a combination of an immunogenic portion from each protein.

The invention also relates to a method of treating or preventing melioidosis in a patient, typically a human patient, comprising a step of administering to the patient a therapeutically effective amount of OMPW, or an immunogenic portion thereof.

The invention also relates to a method of treating or preventing glanders in a mammal, typically an equine mammal such as a horse, comprising a step of administering to the mammal a therapeutically effective amount of OMPW, or an immunogenic portion thereof.

The invention also relates to a DNA vaccine comprising an active agent, a pharmaceutically acceptable carrier, and optionally an adjuvant, wherein the active agent comprises a nucleic acid encoding linocin or OMPW, for example: a nucleic acid encoding a polypeptide of SEQUENCE ID NO:1, or a therapeutically effective variant thereof having at least 90% sequence identity with SEQUENCE ID NO: 1; a nucleic acid encoding a polypeptide of SEQUENCE ID NO:3, or a therapeutically effective variant thereof having at least 90% sequence identity with SEQUENCE ID NO: 3; or a nucleic acid encoding an immunogenic portion of the polypeptide of SEQUENCE ID NO:1 or SEQUENCE ID NO:3.

The invention also relates to a nucleic acid construct comprising a nucleic acid encoding linocin and/or OMPW, and preferably encoding (a) a polypeptide of SEQUENCE ID NO:1, or a therapeutically effective variant thereof having at least 90% sequence identity with SEQUENCE ID NO: 1, fused to a polypeptide of SEQUENCE ID NO:3, or a therapeutically effective variant thereof having at least 90% sequence identity with SEQUENCE ID NO: 1, or (b) an immunogenic portion of the polypeptide of SEQUENCE ID NO:1 fused to an immunogenic portion of the polypeptide of SEQUENCE ID NO:3.

The invention also relates to a fusion protein comprising (a) a polypeptide of SEQUENCE ID NO:1, or a therapeutically effective variant thereof having at least 90% sequence identity with SEQUENCE ID NO: 1, fused to a polypeptide of SEQUENCE ID NO:3, or a therapeutically effective variant thereof having at least 90% sequence identity with SEQUENCE ID NO: 1, or (b) an immunogenic portion of the polypeptide of SEQUENCE ID NO:1 fused to an immunogenic portion of the polypeptide of SEQUENCE ID NO:3, or (c) a polypeptide of SEQUENCE ID NO:1 fused to an immunogenic portion of the polypeptide of SEQUENCE ID NO:3, or (d) a polypeptide of SEQUENCE ID NO:3 fused to an immunogenic portion of the polypeptide of SEQUENCE ID NO:1.

The invention also relates to a diagnostic reagent comprising, or consisting essentially of, Linocin, OMPW, or an immunogenic portion thereof, or an antibody that binds specifically to Linocin, OMPW or an immunogenic portion thereof.

DEFINITIONS

In this specification, the term "Bcc complex" refers to a group of 17 species of Gram negative bacteria [1-3], two of which, *B. multivorans* and *B. cenocepacia*, are particularly virulent [4].

In this specification, the term "infection by a *Burkholderia* pathogen" or "*Burkholderia* infection" should be understood to mean infections of mammals that are caused by a pathogenic strain of *Burkholderia*. Examples of *Burkholderia* pathogens include *B. multivorans*, *B. cenocepacia*, *B. pseudomallei* and *B. mallei*. *B. multivorans* and/or *B. cenocepacia* form part of the Bcc complex which is known to cause chronic lung infection, especially chronic lung infection in immunocompromised patients such as patients with cystic fibrosis or chronic granulomatous disease, and is also implicated in nosocomial (hospital acquired) infection. *Burkholderia pseudomallei*, the causative agent of melioidosis, is a Gram-negative, intracellular pathogen endemic in Southeast Asia and Northern Australia. The disease is considerably variable in humans ranging from acute septicaemia, pneumonia to chronic or latent infection which can persist and emerge decades later. *B. mallei* is an obligate pathogen which causes glanders in horses.

In this specification, the term "infection by Bcc in a patient" should be understood to mean infections caused by *B. multivorans* and/or *B. cenocepacia* and/or any member of the *B. cepacia* complex, especially *B. multivorans* and/or *B. cenocepacia*, including chronic lung infection, especially chronic lung infection in immunocompromised patients such as patients with cystic fibrosis or chronic granulomatous disease, or patients with hospital acquired infection.

In this specification, the term "Linocin" refers to a membrane protein that is expressed by clinically relevant strains of *B. multivorans* and *B. cenocepacia*, for example *B. multivorans* strains, LMG13010 and C1962, and *B. cenocepacia* strains, BC-7 (rec IIIA lineage) and C1394 (rec IIIB lineage). The protein has an approximate molecular weight of 29 kDa, and an approximate PI of 4.8. The amino acid sequence of Linocin_M18 bacteriocin protein expressed by *B. multivorans* strain, ATCC 17616 is provided SEQUENCE ID NO: 1 (FIG. 1A). The nucleic acid sequence encoding Linocin_M18 bacteriocin protein expressed by *B. multivorans* strain, ATCC 17616 is provided SEQUENCE ID NO:

2 (FIG. 1B). The term Linocin encompasses this protein and therapeutically effective variants that share at least 90%, 91%, 92%, 93%, 94%, 95%, 96%, 97%, 98% or 99% sequence homology with SEQUENCE ID NO: 1.

In this specification, the term "OMPW" refers to an outer membrane protein that is expressed by clinically relevant strains of *B. multivorans* and *B. cenocepacia*, for example *B. multivorans* strains, LMG13010 and C1962, and *B. cenocepacia* strains, BC-7 (rec IIIA lineage) and C1394 (rec IIIB lineage). The protein is also expressed by *B. mallei* and *B. pseudomallei*. The protein has an approximate molecular weight of 22 kDa, and an approximate PI of 7.8 to 9. The amino acid sequence of OMPW expressed by *B. multivorans* strain, ATCC 17616 is provided SEQUENCE ID NO: 3 (FIG. 2A). The nucleic acid sequence of OMPW expressed by *B. multivorans* strain, ATCC 17616 is provided SEQUENCE ID NO: 4 (FIG. 2B). The term OMPW encompasses this protein and therapeutically effective variants that share at least 90%, 91%, 92%, 93%, 94%, 95%, 96%, 97%, 98% or 99% sequence homology with SEQUENCE ID NO: 3. The amino acid sequence of OMPW protein expressed by *B. cenocepacia* strain MCO-3 is identical to the sequence provided in SEQUENCE ID NO: 3.

In this specification, the term "therapeutically effective variant" as applied to Linocin means a protein that shares at least 90% sequence homology with SEQUENCE ID NO: 1 and that is capable of eliciting a protective immune response in a mammal immunised with the variant against subsequent challenge by *B. cenocepacia* and *B. multivorans* as described below.

In this specification, the term "therapeutically effective variant" as applied to OMPW means a protein that shares at least 90% sequence homology with SEQUENCE ID NO: 3 and that is capable of eliciting a protective immune response in a mammal immunised with the variant against subsequent challenge by *B. cenocepacia* and *B. multivorans* as described below.

The term "sequence homology" should be understood to mean sequence identity and similarity, i.e. a polypeptide sequence that shares 90% sequence identity with SEQUENCE ID NO: 1 is one in which any 90% of aligned residues are either identical to, or conservative substitutions of, the corresponding residues in SEQUENCE ID NO: 1. Preferably the term means sequence identity. Sequence homology can be calculated by a BLAST program (www.ncbi.nim.nih.gov/cgi-bin Blast).

In this specification, the term "immunogenic portion thereof" as applied to Linocin should be understood to mean a portion of Linocin (i.e. a peptide or polypeptide) that when administered to an animal or human using the methods described below elicits an IgG immune response that is specific to the peptide or polypeptide that is administered. Likewise, the term "immunogenic portion thereof" as applied to OMPW should be understood to a portion of OMPW (i.e. a peptide or polypeptide) that when administered to an animal or human using the methods described below elicits an IgG immune response that is specific to the peptide or polypeptide that is administered.

In this specification, the term "cystic fibrosis" should be understood to an autosomal recessive genetic disorder that effects the lungs of a patient and is characterised by abnormal transport of chloride and sodium across lung cell epithelia leading to thick viscous secretions.

In this specification, the term "Chronic granulomatous disease" should be understood as a group of hereditary immunodeficiency diseases in which the immune cells are unable to kill certain intracellular bacterial pathogens and fungi.

In this specification, the term "vaccine therapy" should be understood to mean the administration of an immunogenic peptide or protein to a mammal with a view to eliciting a response by the host immune system that results in the peptide or protein being destroyed and subsequently recognised by the host immune system In this specification, the term "immune response" should be understood to mean induced humoral or cellular response in the host.

In this specification, the term "vaccine" should be understood to mean a composition comprising at least an immunogenic peptide or protein and optionally a suitable adjuvant and/or carrier. The preparation of vaccines comprising peptide or proteins as active agent is well described in the literature, for example U.S. Pat. Nos. 4,599,230 and 4,601,903, the complete contents of which are incorporated herein by reference.

The term "DNA vaccine" should be understood to mean a composition that comprises a nucleic acid construct capable of being delivered to a patient and expressing in the patient linocin or an immunogenic portion of linocin, OMPW or an immunogenic portion of OMPW, linocin and OMPW, an immunogenic portion of linocin and OMPW, OMPW and an immunogenic portion of linocin, or linocin and an immunogenic portion of OMPW. The antigens may be expressed as separate protein/peptides or in the form of a fusion protein. The vaccine may also include a suitable adjuvant, a pharmaceutically acceptable carrier, or both. The nucleic acid construct is preferably in the form of an expression vector, the detail of which will be known to those skilled in the art, for example a plasmid or a virus such as a lentivirus. DNA vaccines are discussed in detail in Kutzler et al [28].

In this specification, the term "adjuvant" should be understood to mean an agent that enhances the recipient's immune response to an immunogenic peptide or protein. Details of suitable adjuvant compositions are well known to those skilled in the art.

In this specification, the term "immunogenic composition" refers to a composition comprising Linocin or OMPW, or an immunogenic portion of either, that is capable of inducing an immune response in an individual currently or previously infected with Bcc.

Proteins and polypeptides (including variants and fragments thereof) of and for use in the invention may be generated wholly or partly by chemical synthesis or by expression from nucleic acid. The proteins and peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984).

In this specification the term "amount effective" or "therapeutically effective amount" should be taken to mean an amount which results in a clinically significant reduction or prevention of *Burkholderia* infection. Suitably, the immunogenic component of the vaccine is administered at a dose of between 1 microgram and 10 miligrams per ml, preferably between 10 micrograms and 5 miligrams per ml, more preferably between 100 micrograms and 2 miligrams per ml. Typically, it is given as a bolus dose. In the context of the therapeutic aspects of the present invention, the term "individual in need thereof" shall be taken to mean a mammal, preferably a human, who has an infection caused by a pathogenic Burkholderia strain, for example B. multivorans, B. cenocepacia, B. pseudomallei and B. mallei infection.

Suitably, the individual has a chronic Bcc lung infection, and in many cases is a patient with cystic fibrosis or Chronic granulomatous disease, who also has a Bcc lung infection.

The present invention also provides pharmaceutical compositions. Such compositions comprise a therapeutically effective amount of the therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

Various delivery systems are known and can be used to administer a therapeutic of the invention, e.g., intra-nasally. Methods of introduction include but are not limited to intradermal, intramuscular, intraperitoneal, intravenous, subcutaneous, intranasal, epidural, intranasal, intracerebral, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with adjuvants and or other biologically active agents. Administration can be systemic or local. In addition, it may be desirable to introduce the compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

Linocin or OMPW antibodies may be produced using methods which are generally known in the art. In particular, purified Linocin or OMPW may be used to produce antibodies. Antibodies to Linocin or OMPW, or immunogenic portions thereof, may also be generated using methods that are well known in the art. Such antibodies may include, but are not limited to, polyclonal, monoclonal, chimeric, and single chain antibodies, Fab fragments, and fragments produced by a Fab expression library. For the production of antibodies, various hosts including goats, rabbits, rats, mice, camels, dromedaries, llamas, humans, and others may be immunized by injection with Linocin or OMPW or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol.

It is preferred that the oligopeptides, peptides, or fragments used to induce antibodies to Linocin or OMPW have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of Linocin or OMPW amino acids may be fused with those of another protein, such as KLH, and antibodies to the chimeric molecule may be produced. Monoclonal antibodies to Linocin or OMPW may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. USA 80:2026-2030; and Cole, S. P. et al. (1984) Mol. Cell. Biol. 62:109-120.)

In addition, techniques developed for the production of "chimeric antibodies", such as the splicing of mouse antibody genes to human antibody genes to obtain a molecule with appropriate antigen specificity and biological activity, can be used (see, e.g., Morrison, S. L. et al. (1984) Proc. Natl. Acad. Sci. USA 81:6851-6855; Neuberger, M. S. et al. (1984) Nature 312:604-608; and Takeda, S. et al. (1985) Nature 314:452-454). Alternatively, techniques described for the production of single chain antibodies may be adapted, using methods known in the art, to produce Linocin or OMPW-specific single chain antibodies. Antibodies with related specificity, but of distinct idiotypic composition, may be generated by chain shuffling from random combinatorial immunoglobulin libraries (see, e.g., Burton, D. R. (1991) Proc. Natl. Acad. Sci. USA 88:10134-10137.). Antibodies may also be produced by inducing in vivo production in the lymphocyte population or by screening immunoglobulin libraries or panels of highly specific binding reagents as disclosed in the literature (see, e.g., Orlandi, R. et al. (1989) Proc. Natl. Acad. Sci. USA 86:3833-3837; Winter, G. et al. (1991) Nature 349:293-299).

Antibody fragments which contain specific binding sites for Linocin or OMPW may also be generated. For example, such fragments include, but are not limited to, F(ab')$_2$ fragments produced by pepsin digestion of the antibody molecule and Fab fragments generated by reducing the disulfide bridges of the F(ab')$_2$ fragments. Alternatively, Fab expression libraries may be constructed to allow rapid and easy identification of monoclonal Fab fragments with the desired specificity (see, e.g., Huse, W. D. et al. (1989) Science 246:1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between Linocin or OMPW and its specific antibody. A two-site, monoclonal-based immunoassay utilizing monoclonal antibodies reactive to two non-interfering Linocin or OMPW epitopes is generally used, but a competitive binding assay may also be employed. Various methods such as Scatchard analysis in conjunction with radioimmunoassay techniques may be used to assess the affinity of antibodies for Linocin or OMPW. Affinity is expressed as an association constant, $K_a$, which is defined as the molar concentration of Linocin or OMPW-antibody complex divided by the molar concentrations of free antigen and free antibody under equilibrium conditions. The $K_a$ determined for a preparation of polyclonal antibodies, which are heterogeneous in their affinities for multiple Linocin or OMPW epitopes, represents the average affinity, or avidity, of the antibodies for Linocin or OMPW. The $K_a$ determined for a preparation of monoclonal antibodies, which are monospecific for a particular Linocin or OMPW epitope, represents a true measure of affinity. High-affinity antibody preparations with $K_a$ ranging from about $10^9$ to $10^{12}$ L/mole are preferred for use in immunoassays in which the Linocin or OMPW-antibody complex must withstand rigorous manipulations.

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is generally employed in procedures requiring precipitation of Linocin or OMPW-antibody complexes. Procedures for evaluating antibody specificity, titer, and avidity, and guidelines for antibody quality and usage in various applications, are generally available.

BRIEF DESCRIPTION OF THE FIGURES

FIG. 1A. Amino acid sequence of Linocin protein expressed by B. multivorans strain, ATCC 17616 (SEQUENCE ID NO: 1)

FIG. 1B. Nucleic acid sequence of Linocin protein expressed by *B. multivorans* strain, ATCC 17616 (SEQUENCE ID NO: 2)

FIG. 2A. Amino acid sequence of OMPW protein expressed by *B. multivorans* strain, ATCC 17616 (SEQUENCE ID NO: 3).

FIG. 2B. Nucleic acid sequence of OMPW protein expressed by *B. multivorans* strain, ATCC 17616 (SEQUENCE ID NO: 4).

FIG. 3. Representative (Confocal microscopy) images of Bcc attachment in CFBE-cells visualised 60× objective lens. The bacteria were labelled with FITC labelled antibody (green) and cells stained with DAPI (blue). Representative images from *B. cenocepacia* strains BC7 (A); C1394 (B) and *B. multivorans* strains LMG13010 (C); and C1962 (D).

FIG. 4. Attachment of Bcc to CFBE cells (A) and HBE cells (B) were shown in the diagram. Each bar represents mean (±SEM) of two experiments. Blue bars MOI 10:1; Red bars, MOI 50:1.

FIG. 5: Attachment of recombinant *E. coli* expressing Linocin (B) or OMPW (D) to CFBE cells by confocal microscopy compared with wild type *E. coli* (A, C). The bacteria were stained red with Syto 85 dye. Nuclei were stained with Dapi (blue). Some leaching of the dye from the bacteria results in red/purple staining in the nuclei, however, bacteria are clearly observed attached to to the outside of the cells in B and D.

FIG. 6: Protection of mice following immunisation with Linocin. Bacterial CFU were counted in lung (A) and spleen (B) homogenates from triplicate plates prepared individually from groups of 5 mice. Each immunisation study was carried out two independent times. * Statistical significance, $P<0.05$.

FIG. 7: Protection of mice following immunisation with OmpW. Bacterial CFU were counted in lung (A) and spleen (B) homogenates from triplicate plates prepared individually from groups of 5 mice. Each immunisation study was carried out two independent times. * Statistical significance, $P<0.05$.

FIG. 8: Serum antibody responses against Linocin and OmpW in response to immunization. ELISA results of the IgG responses in serum post-immunisation are presented as mean end-point titres in individual sera+/−standard deviation.

DETAILED DESCRIPTION OF THE INVENTION

Two membrane proteins that are involved in attachment of *B. cenocepacia* and *B. multivorans* strains to lung epithelial cells are described, Linocin, a 29 kDa protein and OMPW (22 kDa protein). These proteins have been shown to produce a pronounced immunogenic response in CF patients, as determined by probing 2-D blots prepared from Bcc membrane proteins with serum from patients colonised with Bcc. Both proteins were shown to protect mice from both *B. cenocepacia* and *B. multivorans* challenge and elicit potent humoral antigen-specific responses.

EXPERIMENTAL

Bacterial strains and culture conditions. The four bacterial strains used, two *B. multivorans* strains, LMG13010 and C1962, and two *B. cenocepacia* strains, BC-7 (rec IIIA lineage) and C1394 (rec IIIB lineage), are detailed in Table 1 and were obtained from the BCCM/LMG, University of Ghent, Belgium and routinely plated on *B. cepacia* specific agar (BCSA)[16]. All the bacterial strains were routinely grown in Luria Bertani (LB broth) at 37° C. with orbital shaking (150 rpm). The bacterial cultures were prepared in 10 L fermenter for the large scale isolation of membrane proteins. Overnight 500 ml of bacterial cultures, grown at 37° C. incubator on a shaker at 150 rpm, were inoculated into 10 L LB media. The culture was grown at 37° C., 150 rpm, without pH control or anti-foam control with an air supply of 6 L/min. Bacterial cultures in stationary phase (O.D at 1.0) were used for membrane protein extraction.

Cell Culture: 16HBE14o- (HBE) and CFBE41o- (CFBE) cells were a generous gift from Dr. Dieter Gruenert (UCSF California). The human bronchial epithelial cell line (HBE) was grown in Eagle's Minimal essential medium (EMEM) with 10% FBS, 1% penicillin/streptomycin, 1 L-glutamine, 1% sodium pyruvate and incubated in a 5% $CO_2$ environment at 37° C. [17]. The CFBE cells were grown in MEM medium with 10% FBS, 1% penicillin/streptomycin, 1% L-glutamine, 1% sodium pyruvate, and 1% non-essential amino acids incubated in 5% $CO_2$ environment at 37° C.

Attachment of bacteria to epithelial cells. In order to visually examine attachment of Bcc strains to lung epithelial cells, HBE and CFBE cells were seeded in coated chamber slides for 24 h prior to incubation individually with one of the following: B. cenocepacia strains BC7 or C1394 or B. multivorans strains LMG13010 or C1962 for 30 min at a multiplicity of infection (MOI) of 50:1 or 10:1. Cells were gently washed three times with 1×PBS for five min each and fixed with 3% paraformaldehyde for 10 min at room temperature. The cells were then incubated with 5% BSA in PBS at room temperature for 1 h to block non-specific binding. After blocking, the samples were incubated with primary polyclonal anti-Bcc antibody overnight at 4° C. and bound antibodies were detected with FITC labelled secondary antibody (1:100) for 1 h at room temperature in the dark. Cells were counter-stained with DAPI for 15 min at room temperature in the dark and visualised under fluorescence and confocal microscopy to count the bacteria attached on the cells.

Figure 6A:
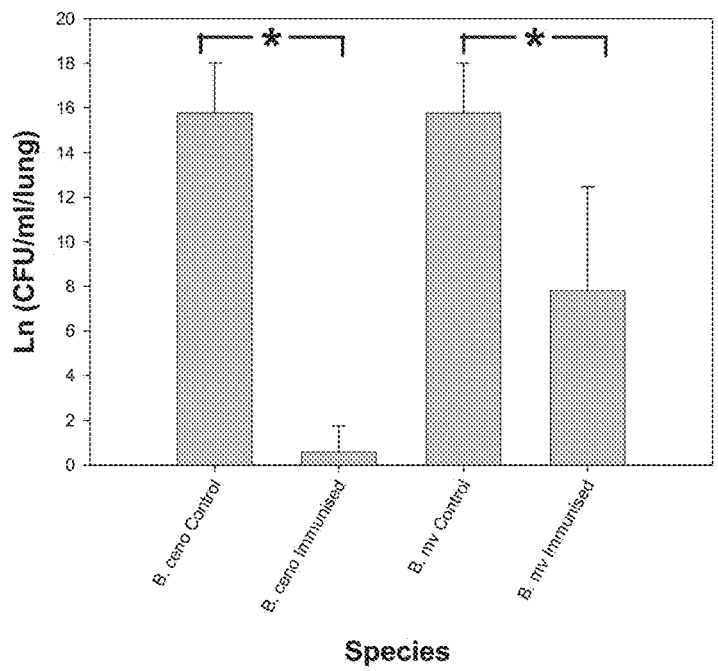

Preparation of bacterial membrane proteins: In order to extract bacterial membrane proteins, bacteria were cultured in a 10 L fermenter overnight at 37° C., 150 rpm, without anti-foam control with an air supply of 6 L/min. When the bacterial culture had reached stationary phase (O.D at 1.0) the cells were collected by centrifugation for membrane protein extraction by a modified method of Plesa et al., [18]. After centrifugation at 6,000 rpm for 10 min at 4° C., the pellet was resuspended in ice cold PBS contains 5% CHAPS and 5% protease inhibitor cocktail. An additional centrifugation step at 5,000 g for 10 min at 4° C. was carried out to eliminate unbroken cells and debris. The supernatant was ultracentrifuged at 30,000 g at 4° C. for 30 min and the pellet was resuspended in 10 ml of 2 mM $MgCl_2$, 50 mM Tris (pH 8) containing 5% protease inhibitor cocktail and centrifuged in the same conditions. The new pellet was resuspended in 2% triton X-100, 50 mM Tris (pH 8) with 5% protease inhibitor cocktail and incubated for 30 min at 40° C. with gentle shaking. The ultracentrifugation was repeated for another hour and the pellet was washed with 50 mM Tris (pH8) buffer with 5% protease inhibitors and ultracentrifuged in the same conditions and the final pellet was resuspended in 50 mM Tris, pH8. The protein concentration was determined by Bicinchoninic acid assay (BCA) or Bradford assay.

Two dimensional electrophoresis. The membrane proteins were solubilised for isoelectric focusing (IEF) in a rehydration solution containing 8 M urea, 2 M thiourea, 4% CHAPS, 1% Triton, 10 mM Trisbase, 65 mM DTT and 0.8% (v/v) IPG buffer (pH 3-11NL) and a trace of bromophenol blue. IPG dry strips (pH 3-11) NL of 7 cm were rehydrated overnight with 120 µl of the rehydration solution containing 120 µg of proteins. The IEF step was carried out for 3 h focusing with a total voltage of 7,000V applied. Following IEF, the IPG strips were equilibrated in reducing buffer for 20 min under agitation at room temperature in 30% glycerol, 2% SDS, 6 M urea, 50 mM Tris and 2% DTT. The IPG strips were then alkylated by a further 20 min equilibration in same buffer containing 2.5% iodoacetamide instead of DTT and a trace of bromophenol blue. The IPG strips were placed on 12% SDS-PAGE gels and the separation was carried out at 110 V. The proteins were detected by using Coomassie blue stain.

Cell attachment Blots: Prior to transfer of the proteins from gel to the membrane, the gel was equilibrated in the transfer buffer (25 mM (w/v) Tris, 192 mM (w/v) glycine, 20% (v/v) methanol [19] together with blotting paper and for 15 min Immobilon-P transfer membrane was serially dipped in methanol for 3 sec, distilled water for 2 min, and transfer buffer for 3 min. The protein transfer was carried out in a Transphor unit (Bio-Rad) at 330 mA for 50 min and blocked overnight with 5% BSA in PBS at 4° C. on a shaker at 10 rpm. Lung epithelial cells (either CFBE or 16 HBE) were scraped from flasks, washed with PBS and incubated with the membrane for 4 h at 37° C. on a shaker at 60 rpm. The membranes were rinsed with 20 ml of PBS, and the bound epithelial cells were fixed with 3% paraformaldehyde dissolved in PBS. The cells were detected with anti-epithelial antibody. After incubation with cells, the membrane was then incubated with mouse anti-epithelial cell antibody (1:1,000 in 5% (w/v) BSA 0.04% (w/v) PBS-T) overnight at 4° C. on a shaker at 10 rpm. The membrane was then washed three times and incubated with HRP conjugated anti mouse antibody (1:40,000 in 5% (w/v) BSA 0.04% (w/v) PBS-T) at room temperature. The membrane was then washed five times and chemiluminescence detection was carried out by using the Santa-Cruz luminol detection kit.

Immunoblot of Membrane Proteins from Bcc with CF Patient Sera

Two dimensional blots were incubated with pooled serum from seven CF patients that had been positively identified with a Bcc infection. Control blots were probed with serum from six CF patients that were negative for Bcc infection. In both cases, the serum was diluted to 1:8,000, incubated for 1 h and washed with PBST (0.05% Tween-20) three times. Then the blots were then incubated with HRP conjugated anti-human IgG Ab (1:16,000) and washed again with PBST (0.4%) five times. Chemiluminescence detection was carried out by incubating the membranes for 5 min with Santa-Cruz luminol detection kit and followed by exposure to Kodak photosensitive film for 30 sec to 2 min followed by development using Kodak developer and fixing solutions.

MALDI-ToF MS/MS analysis: Protein spots excised from 2D gels were destained with an equal volume of 100 mM ammonium bicarbonate and acetonitrile. Gel digestion was performed with 13 ng/µl of modified porcine trypsin for 2 h in an ice bucket followed by overnight incubation of samples at 37° C. in an air circulation thermostat. Tubes were chilled to room temperature, and gel pieces pelleted using a micro-centrifuge. Aliquots of 2 to 2.5 µl of the supernatant were withdrawn directly from the digest for MALDI-ToF MS/MS analysis, without further extraction of the gel pieces [20]. MALDI analysis was performed using a Bruker Ultraflex MALDI-ToF (Bruker Daltonics) with ground steel target plate. An equal volume of (1:1) peptide extracts and matrix solution (2 mg/ml α-cyano-4-hydroxycinnamic acid (CHCA) in 70% of 0.1% TFA and 30% of acetonitrile) were applied on to the target plate along with peptide calibration standards and BSA as a control and then all samples were allowed to dry.

Peptide Mass Fingerprinting (PMF) was used for protein identification and the spectra were analysed in Flex Analysis and BioTools software from Bruker. Peak lists were then submitted to the MASCOT (http://www.matrixscience.com) search engine for analysis.

Protein sequence database searching was performed on the NCBInr database. The following general search parameters were used: monoisotopic molecular masses, enzyme specificity trypsin, all species allowed, variable modification was methionine oxidation and global modification was carbamidomethyl cysteine alkylation, with a mass tolerance of 100 ppm.

Cloning and Expression of membrane proteins: Genomic DNA was isolated using the DNeasy® Blood & Tissue kit from Qiagen. The specific primers were designed according to Linocin and OmpW sequences of B. multivorans strain, ATCC 17616, and B. cenocepacia strain, MCO-3, from NCBI. To enable the directional cloning the forward primers contained CACC sequence at the 5' end. The sequences of the forward and reverse primers for amplification are shown in Table 1. PCR amplification was carried out with Hot start high-fidelity PCR kit from Qiagen using the following thermal cycle programme: initial activation for 5 min at 95° C., followed by 35 cycles consisting of denaturation at 94° C. for 30 sec, annealing at 50-68° C. for 30 sec, and the extension at 72° C. for 30 sec. For the last cycle, the incubation period at 72° C. was extended to 5 min and maintained at 4° C.

The overnight bacterial culture used for extracting the plasmids. A single colony was inoculated in LB contain ampicillin and grow overnight for extracting the plasmids. Plasmid DNA was islolated using the QIAprep Spin Miniprep Kit (Qiagen), according to manufacturer's instructions. The plasmid DNA was restriction digested in a reaction which consisted of up to 1 μg of prepared DNA, 10× restriction enzyme digestion buffer, 1 μl restriction enzymes and ultrapure water. The reaction was mixed and incubated at 37° C. for 15 min and then digest products were subjected to agarose gel electrophoresis to visualise.

Cloning and Expression: Primers were designed for pET 100 vector and amplified with AccuPrime Taq DNA polymerase. Following agarose gel analysis of product integrity, the cloning reaction mixture was prepared using fresh PCR product in a final volume of 6 μl with a final PCR product: TOPO® vector ratio of 0.5:1 to 2:1. The PCR product and the TOPO vector were incubated at room temperature for 5 min. The pET TOPO® construct was transformed into One Shot TOP 10 Chemically Competent E. coli by adding the cloning reaction mixture and incubating on ice for 30 min. The cells were heat shocked for 30 sec at 42° C. without shaking and 250 ul of SOC medium (2% Tryptone, 0.5% Yeast Extract, 10 mM NaCl, 2.5 mM KCl, 10 mM MgCl2, 10 mM MgSO4 and 20 mM glucose) was added and incubated at 37° C. for 1 hr with shaking. The culture was then spread on LB agar plates with ampicillin (100 ug/ml) and incubated overnight at 37° C. The positive transformants were analysed by using colony PCR or by restriction digestion.

Transforming BL21 Star™ (DE3) One Shot Cell: BL21 Star™ (DE3) One Shot E. coli was used as the host for expression. The plasmid isolated from positive clones was transformed into BL21 Star™ cells. An aliquot of 5-10 ng of plasmid DNA was added in each vial of BL21 Star cells, mixed and incubated on ice for 30 min. The cells were then heat-shocked for 30 sec at 42° C. without shaking and then transferred to ice. SOC medium (250 μl) was added to the cells and incubated at 37° C. with shaking (225 rpm). After 30 min the entire transformation reaction was added to 10 ml of LB containing ampicillin (100 μg/ml) and grown overnight at 37° C. with shaking.

Large Scale expression of recombinant protein: A culture of BL21 cells (1 L to 1.5 L) containing the plasmid of interest was grown in LB with ampicillin (100 μg/ml) and induced with appropriate IPTG concentration to the optimal optical density. The expression was included with appropriate IPTG concentration. The culture was then centrifuged at 5,000 rpm for 10 min and the pellet was frozen at −80° C. until needed.

Recombinant Protein Extraction: The expressed bacterial proteins were extracted by adding lysozyme, DNase and EDTA free protease inhibitor to bacterial pellets and incubating for 10-15 min at room temperature. The lysate was centrifuged at 15,000×g for 5 minutes to separate soluble proteins from the insoluble proteins.

Purification of His-tagged recombinant protein using Ni-NTA column: HisPur Ni-NTA spin columns (Thermo scientific) were used to purify polyhistidine-tagged proteins from the protein extract. The samples were mixed with equal volume of equilibration buffer and spun down in the Ni-NTA column. The columns were washed three times with wash buffer containing 25 mM imidazole. After washing the column the samples were then eluted with 250 mM imidazole and the fractions were analysed by SDS-PAGE. The purified recombinant protein was desalted with Zeba™ spin desalting column (Thermo scientific). The desalted samples were collected and stored at −80° C. for further purification.

Endotoxin removal from purified protein: Detoxi® gel endotoxin removal columns (Thermo scientific) were used to remove the endotoxins from the recombinant protein. The columns were degenerated with 1% sodium deoxycholate, and washed with non-pyrogenic water. The protein samples were applied on the column and the flow-through were collected and kept at −80° C. ToxinSensor™ Gel Clot Endotoxin Assay Kit (GenScript) was used to determine the endotoxin level in the purified protein. The assay was done as described in the assay kit manual. The positive reaction was characterized by the formation of a firm gel that remains intact when the vial is inverted. The negative reaction is characterized by the absence of a solid clot. The lysate may show an increased turbidity or viscosity. This is considered a negative result. The endotoxin level in the positive sample is equal to or higher than 0.25 EU/ml; while in the negative sample, the endotoxin level is lower than 0.25 EU/ml.

Immunisation of recombinant protein: Pathogen free BALB/c mice (females 6-8 weeks old) were housed in groups of five in standard pathogen-free conditions with food and water available. The mice (n=5 per group) were vaccinated with two administrations of either vaccine, four weeks apart. Intraperitoneal (i p) immunizations were performed with 50 ng of recombinant protein per mouse and an equal volume of inject Alum (Pierce scientific). The bacterial challenge studies were performed in immunized mice two weeks following booster vaccination. The mice were immunosuppressed by i.p injection of 50 ng of cyclophosphamide on day −1 and 4 of challenge. The immunized and non-immunised mice were challenged with $4 \times 10^7$ of BC7 and LMG13010 suspended in 20 nl of PBS instilled intranasally. The mice were then maintained for a period of 5 days before sacrifice by cervical dislocation. The lungs, spleen and the blood were collected in sterile conditions and each organ was placed into individual containers containing 1 ml of Ringers solution. The blood was kept at RT for 4 hrs to clot and then centrifuged at 16,000 rpm for 15 min to collect the serum. The aliquots of serum were then kept at −80° C. for further analysis. The lungs and spleen were homogenized and serially diluted in Ringer's solution and were plated onto BCSA plates. All plates were then incubated for 72 hrs at 37° C. prior to manual CFU enumeration.

Determination of Antigen Specific Antibodies by ELISA

The indirect ELISA was used to evaluate the specific immunogenic effect of recombinant proteins. The Linocin and OmpW specific IgGs were measured using ELISA. The 96-well Nunc-Immuno MaxiSorp assay plates were coated with 2 μg/well of purified antigen, either Linocin or OmpW, in coating buffer (sodium bicarbonate, pH 9.4). After overnight incubation at 4° C., the plates were blocked with 10% BSA in PBS for 1 h at RT. Serial four-fold dilutions of serum in 1% BSA were added (100 μl/well), and the plates were incubated for 2 h at room temperature. After four washes with PBS-0.05% Tween 20, horseradish peroxidase-conjugated goat anti-mouse antibodies (either anti-IgG1, -2a or -2b (Abcam)) were added at 1:5000 in 1% BSA. Following 2 hr incubation at RT, the plates were then washed four times and the reactions were developed with TMB substrate (Pierce, Thermo scientific) and stopped after 20 min with 2M $H_2SO_4$. The absorbance was determined at a wavelength of 450 nm. Serum antibody titres were defined as end-point titres i.e. the reciprocal of the highest dilution of serum producing an OD above the cut-off value, where the cut-off values was determined as the OD of the corresponding dilution of control sera plus three standard deviations.

Visualisation of recombinant bacterial cell attachment to lung cells: The recombinant *E. coli* were fluorescently labelled with Syto 82 as follows: Cultures (O.D$_{600}$=0.7) were pelleted and twice with TBS. The bacterial pellets were then resuspended in 500 μl of TBS containing 15 uM Syto82 (Invitrogen) and incubated for 30 min at 37° C. with 150 rpm. The labelled bacteria were then carefully washed seven times with TBS prior to use. CFBE cells were seeded in 24 h prior to incubation with labelled bacterial strains for 30 min. Cells and bacteria were gently washed three times with TBS for 5 min each and fixed with 3% paraformaldehyde for 10 min at RT. Samples were then mounted with a drop of Vectashield mounting medium contain DAPI and visualized under confocal microscope.

It is evident that all Bcc strains showed over two-fold more attachment to CFBE-cells than to HBE cells (FIG. 2).

Identification of the Proteins Involved in Lung Cell Attachment.

To identify the proteins involved in attachment of Bcc to host cells enriched membrane proteins were prepared from either *B. multivorans* or *B. cenocepacia* strains and analysed on cell-probed blots obtained follow 2-dimensional gel electrophoresis (2-DE). membrane proteins from two different *B. multivorans* strains, LMG13010 and C1962 were prepared and individually analysed. The 2D gel separation of LMG13010 and C1962 membrane proteins showed approximately one hundred and fifty distinct proteins spots which were visible after Coomassie blue staining where most of the spots were found to be in the pH 4-10.5 range. In the CFBE-cell probed blot of LMG13010, six clear spots were identified between 20 kDa-30 kDa regions as being positive for cellular attachment. Two of the excised proteins were identified as Linocin and OmpW (Table 2). Only four spots were identified on HBE probed blot in the region of 20 kDa to 30 kDa, including Linocin, The membrane proteins of *B. cenocepacia* strains BC7 and C1394, piliated and non-piliated respectively, involved in lung cell binding were also identified on cell probed blots

TABLE 1

Primers used for cloning membrane proteins.

| Gene of interest | Bacterial strain used for amplification | Original strain used to prepare primer | Primer sequence 5'-3' | GC Content (%) | Melting Temp (° C.) |
|---|---|---|---|---|---|
| Linocin Forward | BC7, C1394, C1962 & LMG13010 | ATCC17616 | CACCATGAACAATCTG CACCGCGA ACTC (SEQ ID NO: 5) | 53.6 | 63.3 |
| reverse | | | ATCAGGCGGGCGTGCC GGC (SEQ ID NO: 6) | 83.3 | 70.0 |
| OmpW Forward | C1962 & LMG13010 | ATCC17616 | CACCATGCATCAAACC AATGACA (SEQ ID NO: 7) | 43.5 | 56.4 |
| reverse | | | CTAGAACTTCATCCCG ACACC (SEQ ID NO: 8) | 52.4 | 54.8 |
| OmpW | BC7, C1394 | MC0-3 | CACCATGCATAAAACG ATTCGA (SEQ ID NO: 9) | 41.0 | 66.5 |
| Forward | | | CTAGAACTTCATCCCG ACGCC (SEQ ID NO: 10) | 57.2 | 66.9 |

Results

Attachment of Bcc Strains to Lung Epithelial Cells

To compare attachment of different strains of Bcc to lung epithelial cells with and without a CF phenotype, fluorescence microscopy was carried out. CFBE and HBE cells were grown on chamber slides and infected with *B. cenocepacia* strains, BC7, C1394, or *B. multivorans* strains LMG13010 or C1962, at a multiplicity of infection (MOI) of 10:1 or 50:1 for 30 min.

The bacteria were labelled by anti-Bcc polyclonal antibody and identified with a FITC labelled secondary antibody and quantified by counting the number of bacteria per field.

followed by MALDI-TOF/MS analysis. Many of the proteins identified were common to both CFBE and HBE cell probed blots. Nine proteins spots were observed on the C1394 blots while 10 proteins were visible on the BC7 blots. There were eight proteins identified from CFBE probed blots of C1394 membrane proteins and only one protein on the HBE probed blots prepared from this strain. The proteins on the CFBE-probed blots included OmpW family protein and Linocin and were identified with a high sequence coverage (Table 2).

Parallel studies were carried out on *B. cenocepacia* strains, BC7 and C1394. A total of eight proteins were found on membrane protein blots prepared from the piliated *B.*

*cenocepacia* strain BC7 probed with CFBE-cells, which had molecular weights in the range of 20-40 kDa. The identified proteins included Linocin, OmpW family protein. Linocin was also identified in corresponding HBE probed blots.

Linocin and OmpW were common to both *B. cenocepacia* strains BC7 and C1394, and to both *B. multivorans* strains.

TABLE 2

MALDI-Tof analysis of proteins involved in attachment to CFBE cells as identified on 2-D cell-probed blots.

| GI number | Protein name | MW (Da) | Sequence coverage % | pI | Mowse Score |
|---|---|---|---|---|---|
| gi\|161522446 gi\|221198593 gi\|221211796 | linocin_M18 bacteriocin protein | 28999 | 50.2-84.9 | 4.8 | 198-219 |
| gi\|161524680 gi\|221198032 | OmpW family protein | 21033 | 72.4-85.9 | 7.8 | 84-143 |

Investigations of the Immunogenicity of the Membrane Proteins Involved in Bcc Attachment Using CF Patient Sera Having identified the proteins that were involved in attachment to lung epithelial cells, the immunogenicity of these proteins in Bcc colonised CF patients was examined to investigate if the proteins were expressed during human infection and whether they were immunoreactive proteins. The antibody responses to Bcc membrane proteins were investigated by immunoblotting Bcc membrane proteins with sera from Bcc colonised CF patients. Sera from seven CF patients with positive identification of Bcc infection and sera from six CF patients that were identified as negative for Bcc infection were obtained from Dr Kirsten Schaffer, St. Vincent's University Hospital (SVUH). Ethical approval was obtained for working with CF sera from the SVUH Research ethics committee. Two dimensional blots were prepared from each of the four strains as before and probed with either Bcc positive serum. Serum from patients with no history of Bcc colonisation was used as a negative control. All immunoblots probed with Bcc positive sera showed strong antibody response to membrane proteins from all four strains. The corresponding membrane proteins on the gel were analysed by MALDI-TOF/MS. MALDI-TOF/MS identified over 50 proteins as immunogenic. Linocin and OmpW were identified as expressed and immunoreactive in all four strains examined. This shows that these proteins are both expressed by the bacteria during human infection and are exposed to and targeted by the immune system. Both proteins were identified as immunogenic in blots prepared from each of the four strains.

Cloning and immunisation of Linocin and OMPW Both proteins were cloned as described above and expressed in *E. coli*. Prior to purification of the proteins, the affinity of the recombinant *E. coli* for lung epithelial cells were investigated in order to examine whether the expression of these proteins enhanced attachment to lung epithelial cells. In the absence of Linocin, only 0.59% of the expression strain cells, BL21*, were attached to CFBE cells. This increased by 7.4% (12.5-fold increase) for the Linocin expressing recombinant, confirming the role of Linocin in attachment. In addition, the attachment of recombinant *E. coli* expressing OmpW increased by 8.7-fold.

Purification of Linocin and OmpW.

The Linocin and OmpW were purified using Nickel affinity columns, followed by purification on an endotoxin affinity column to remove LPS. The purified protein was confirmed to have an endotoxin level less than 0.25 EU/ml.

Immunisation of Mice.

Two groups of mice (5 mice each) were immunised with linocin formulated with alum (ip) on day 0 and day 28 and subsequently challenged with *B. cenocepacia* or *B. multivorans* two weeks after the final booster.

Figure 6B:
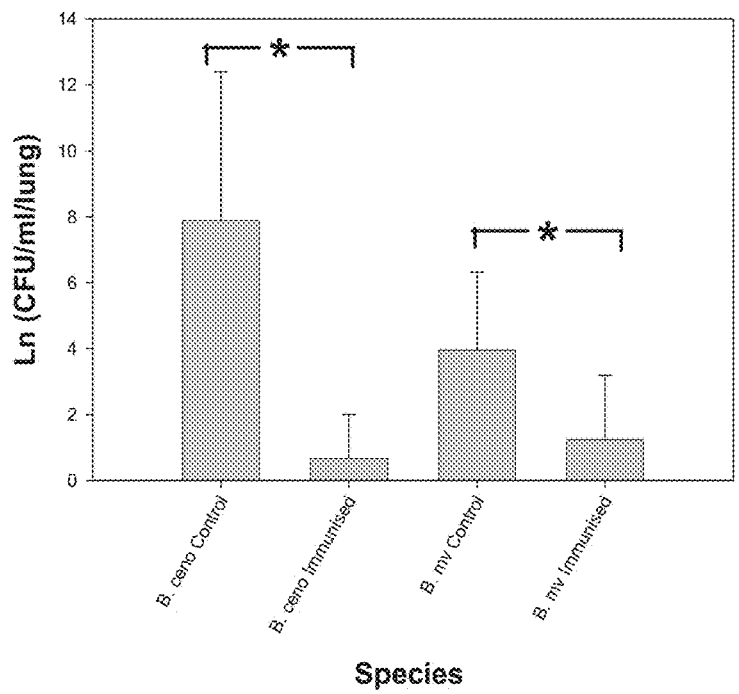

The data from two independent experiments are shown in FIG. 6. It was clear that linocin immunisation protected mice from challenge with *B. cenocepacia* and *B. multivorans*. Immunisation with linocin reduced the *B. cenocepacia* to barely detectable levels (mean value of 3 CFU/ml/lung, P=0) (FIG. 6a). Although the effect on the *B. multivorans* was not as potent, the CFU in the lung reduced by four thousand-fold to the unimmunised controls (P=0.015). Bcc is an invasive pathogen and escapes the lung and colonises the spleen. Immunisation with linocin protected the mice from invasion of *B. cenocepacia* to the spleen to 0.001% of unimmunised controls (P=0) (FIG. 6b). *B. multivorans* is generally less invasive than *B. cenocepacia*, and this was confirmed in this study, where the unimmunised controls showed less splenic invasion than the *B. cenocepacia* controls of the order of five logs. Despite this splenic invasion of *B. multivorans* was reduced following Linocin immunisation to 10% of the unimmunised LMG13010 challenged mice (P<0.018).

Figure 7A:
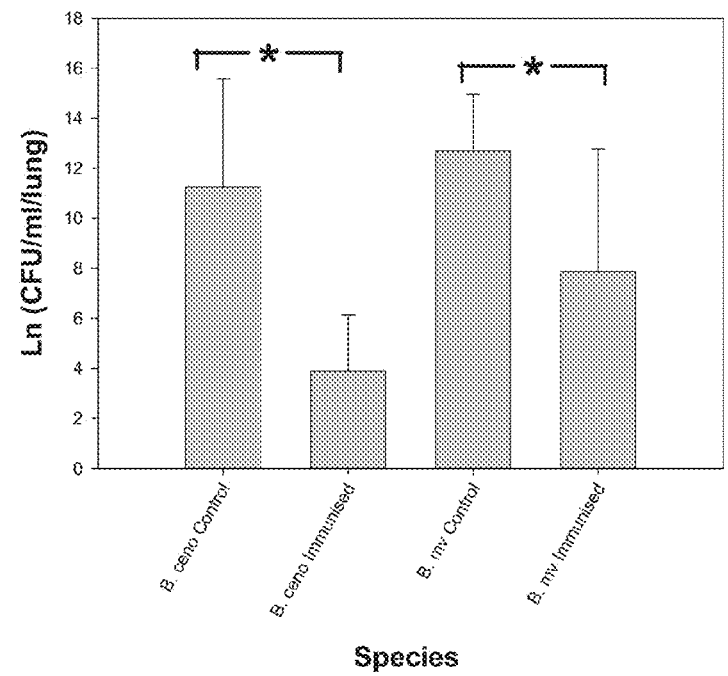
Figure 7B:
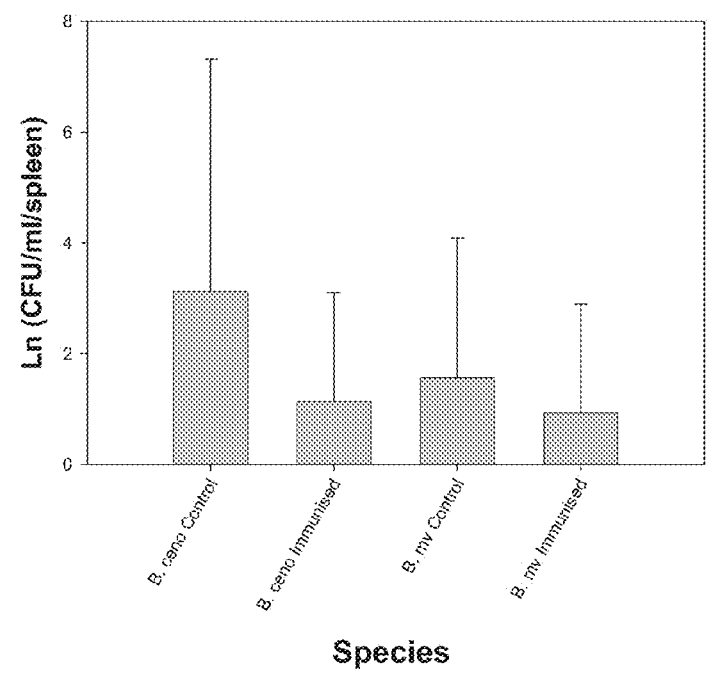

Groups of mice were also immunised with OMPW using the same protocol as that described for Linocin. Again the mice were challenged two weeks after the booster and sacrificed five days later. FIG. 7 shows that the mice were protected against BC7 with a reduction in lung bacterial counts by 7 Ln (60,000 fold reduction in bacterial counts, p=0). OmpW was more effective in protecting mice against *B. multivorans* infection than Linocin Immunisation with OMPW protected against *B. multivorans* by a four-Ln reduction, (P<0.013) (the lung bacterial count reduced to 8% of controls). Splenic invasion was also reduced; however this did not reach statistical significance following OmpW immunisation (FIG. 7b).

Antibody Responses Following Immunisation.

Figure 8:
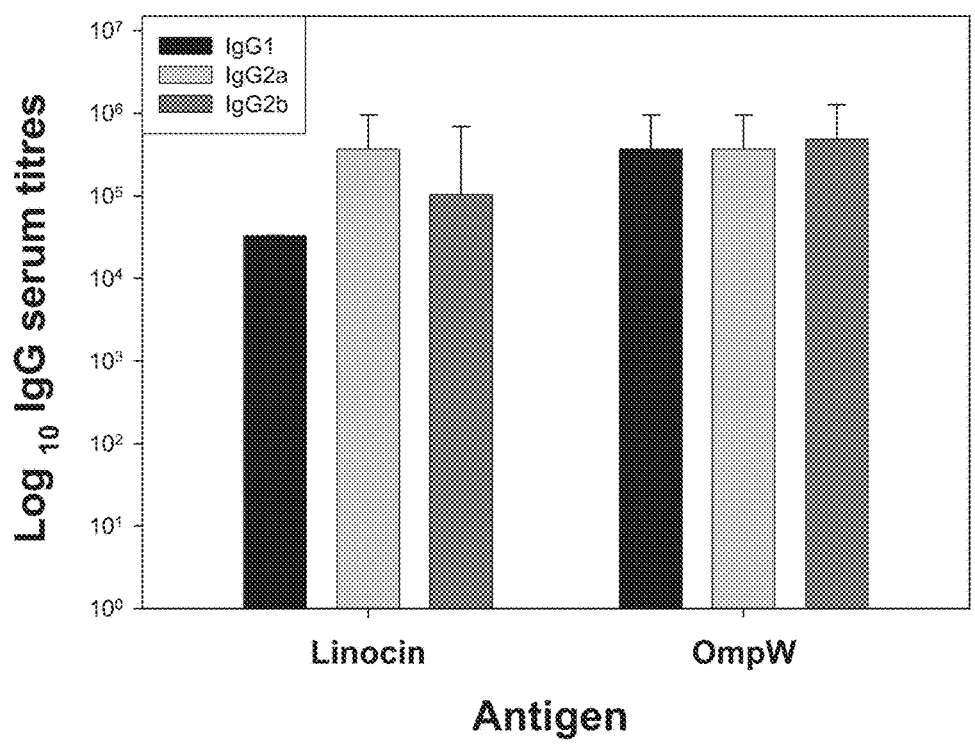

The levels of antigen specific antibodies were measured in the serum of immunised mice relative to controls. Pooled sera from mice in the immunised groups showed high titres of antigen specific IgG1, IgG2a and IgG2b. The ratio of IgG2a to IgG1 antibodies in response to Linocin was indicative of a potent Th1 response in while the ratio IgG2a to IgG1 in response to OmpW was indicative of a mixed Th1/Th2 response (FIG. 8).

The two antigens, Linocin and OMPW have been identified as proteins involved in bacterial attachment to lung epithelial cells. This was confirmed by an increase in attachment of recombinant *E. coli* expressing each of these proteins. Furthermore, CF patients colonised with Bcc produce antibodies which specifically recognise these proteins which demonstrates that these proteins are expressed during human infection and that they are immunoreactive. The use of these proteins as vaccines was demonstrated in mouse immunisation studies, where mice were protected from Bcc challenge following 2 immunisations with either of the antigens. Protection was greatest against *B. cenocepacia* over *B. multivorans*, but lung CFU were reduced in mice immunised with either OMPW and to a greater extent with Linocin.

The invention is not limited to the embodiment hereinbefore described which may be varied in construction and detail without departing from the spirit of the invention.

Testing of the Bivalent Antigen.

A combination of both antigens, OMPW and Linocin, will be co-administered to groups of mice (day 0 and day 28, dose at 10 to 50 μg/mouse). Mice will be immunosuppressed with cyclophosphamide (i.p injection of 50 μg at day 35 and day 40) and intranasal challenge on day 36 with either *B. multivorans* (Groups 1 and 2) or with *B. cenocepacia* (Group 3 and 4).

The protection from these pathogens will be monitored by:
1. Lung CFU in the immunised mice versus lung CFU in control mice as evidence of protection from colonisation.
2. Spleen CFU in immunised mice versus control mice as evidence of protection from invasion
3. Antigen specific IgG1, IgG2a and IgG 2b will be assessed to examine seroconversion and the type of cellular response achieved.
4. Cellular response will also be examined by removing spleen cells and re-exposing them to antigen. Cytokine responses (I1-10, 11-4, 11-6, 11-17) to the antigen will be examined.

Expected outcome—it is expected that both antigens co-administered will give better protection (in terms of reduced levels of bacteria in the lungs and spleens) than either one antigen alone.

Techniques for Fusion Protein.

Fusion proteins of Linocin and OMPW (or epitopes within these) will be constructed by amplifying the relevant gene sequences from both genes by PCR and ligating them to each other or to other *Burkholderia* proteins and into a plasmid for transformation of *E. coli* as outlined by Lubitz and Von Specht et al. [21, 22] and Mansouri et al. [23]. The fusion proteins will be expressed in *E. coli* and purified on nickel affinity columns as described for the individual recombinant antigens described herein. We plan to construct several variations of fusion proteins, with different lengths of constructs of both antigens. For example, constructs from each of the individual extracellular loops of OmpW ligated to the complete linocin sequence etc. These can all be tested in mice to examine which are the most immunogenic and protective.

Route of Administration—Mucosal Vaccination

Previous studies were carried out using alum and intraperitoneal injection. The majority of commercially available vaccines are administered intramuscularly with alum as the adjuvant, therefore this route will be tested. Bcc is predominantly a respiratory pathogen, therefore it is quite likely that mucosal immunisation may give the best protective response. This would require an intranasal route with a mucosal adjuvant such as chitosan in the final formulation. Routes of administration will be evaluated by comparing i.m injection with alum as the adjuvant in both quadriceps muscles with intranasal administration using chitosan as the mucosal adjuvant.

Antigens will be administered singly and in combination at a final volume of 20 ul/mouse with chitosan as the adjuvant for intranasal administration 50 ul/mouse with alum as the adjuvant for intramuscular.

Expected outcome: A strong mucosal response following intranasal administration.

Intranasal Adjuvants:

Chitosan is an excellent mucosal adjuvant suitable for intranasal delivery, giving strong mucosal and systemic responses. It will be milled to reduce the particle size to between 45 an 100 μm. The final formulation containing 1 to 50 ug of lyophilised antigens blended with trehalose and chitosan [24]. Other mucosal adjuvants can include nanoemulsions [25] or adamantylamide dipeptide [26], both of which have been shown to induce pronounced effective mucosal responses in Bcc vaccines. Adamantylamide dipeptide (AdDP, Molecular Formula: $C_{18}H_{30}N_4O_3$ Molecular Weight: 350.46) is typically co-administered at 100 ug/dose together with antigen (10 to 50 ug/dose) in PBS. Typically nanoemulsions are prepared by emulsifying cetyl pyridinium chloride (1%), tween 20 (5%) and ethanol 8% in water with soybean oil (64%) in a high seed emulsifier. This is then vigorously mixed with antigens (between 0.5 and 2.5 mg/ml) at between at 20% (v/v) NE concentrations.

Protection Against *B. pseudomallei.*

Groups of C57BL/6 mice will be administered *B. pseudomallei* OMPW intraperitoneally. Two mouse models will be used which mimic human melioidosis, both acute infections and chronic infections. The mice will be immunised using the Bp antigen (10 to 50 ug per mouse) and rested for 5 weeks before challenge by intranasal exposure to Bp. They will be analysed up to 4 weeks post infection. In the chronic model, the mice will be challenged and studied 8 weeks post infection. The lungs and spleens of mice will be analysed for their bacterial load a week after challenge. Serum samples will be analysed for antigen-specific antibody levels by ELISA, using methods developed previously here.

Expected outcome: Studies will result in a protective response.

DNA Vaccines.

Typically the Linocin and OmpW genes or epitopes from within these genes would be constructed in a plasmid containing T cell epitopes. For example the pIRES-FL plasmid contains the FMS-like tyrosine kinase 3 ligand T cell epitope that induces potent immune responses. This plasmid will be ligated to include one of the following: full-length linocin gene alone, full-length OmpW gene alone, both genes together or combinations of sequences encoding for epitopes from either or both antigens. Additional groups of mice can be also administered 2.5 to bug purified recombinant antigens intranasally, 3 weeks after DNA vaccination (DNA+Ag group) [27].

REFERENCES

1. Coenye, T., et al., *Taxonomy and identification of the Burkholderia cepacia complex*. J Clin Microbiol, 2001. 39(10): p. 3427-36.
2. Coenye, T., et al., *Updated version of the Burkholderia cepacia complex experimental strain panel*. J Clin Microbiol, 2003. 41(6): p. 2797-8.
3. Mahenthiralingam, E., et al., *Multilocus sequence typing breathes life into a microbial metagenome*. PLoS ONE, 2006. 1: p. e17.
4. Mahenthiralingam, E., T. A. Urban, and J. B. Goldberg, *The multifarious, multireplicon Burkholderia cepacia complex*. Nat Rev Microbiol, 2005. 3(2): p. 144-56.
5. Courtney, J. M., et al., *Clinical outcome of Burkholderia cepacia complex infection in cystic fibrosis adults*. J Cyst Fibros, 2004. 3(2): p. 93-8.
6. Chernish, R. N. and S. D. Aaron, *Approach to resistant gram-negative bacterial pulmonary infections in patients with cystic fibrosis*. Curr Opin Pulm Med, 2003. 9(6): p. 509-15.
7. Saiman, L., et al., *Cathelicidin peptides inhibit multiply antibiotic-resistant pathogens from patients with cystic fibrosis*. Antimicrob Agents Chemother, 2001. 45(10): p. 2838-44.
8. Baird, R. M., et al., *Burkholderia cepacia is resistant to the antimicrobial activity of airway epithelial cells*. Immunopharmacology, 1999. 44(3): p. 267-72.
9. McDowell, A., et al., *Epidemiology of Burkholderia cepacia complex* species *recovered from cystic fibrosis* patients: issues related to patient segregation. J Med Microbiol, 2004. 53(Pt 7): p. 663-8.
10. Mahenthiralingam, E., A. Baldwin, and C. G. Dowson, *Burkholderia cepacia complex bacteria: opportunistic pathogens with important natural biology*. J Appl Microbiol, 2008. 104(6): p. 1539-51.
11. Vardi, A., et al., *An outbreak of Burkholderia cepacia bacteremia in hospitalized hematology patients selectively affecting those with acute myeloid leukemia*. Am J Infect Control, 2012.
12. Fishman, J. A., *Infections in immunocompromised hosts and organ transplant recipients: essentials*. Liver Transpl, 2011. 17 Suppl 3: p. S34-7.
13. Caraher, E., et al., *Invasion and biofilm formation of Burkholderia dolosa is comparable with Burkholderia cenocepacia and Burkholderia multivorans*. J Cyst Fibros, 2007. 6(1): p. 49-56.
14. Bertot, G. M., et al., *Nasal immunization with Burkholderia multivorans outer membrane proteins and the mucosal adjuvant adamantylamide dipeptide confers efficient protection against experimental lung infections with B. multivorans and B. cenocepacia*. Infect Immun, 2007. 75(6): p. 2740-52.
15. Makidon, P. E., et al., *Induction of immune response to the 17 kDa OMPA Burkholderia cenocepacia polypeptide and protection against pulmonary infection in mice after nasal vaccination with an OMP nanoemulsion-based vaccine*. Med Microbiol Immunol, 2010. 199(2): p. 81-92.
16. Henry, D. A., et al., *Identification of Burkholderia cepacia isolates from patients with cystic fibrosis and use of a simple new selective medium*. J Clin Microbiol, 1997. 35(3): p. 614-9.
17. Goncz, K. K., L. Feeney, and D. C. Gruenert, *Differential sensitivity of normal and cystic fibrosis airway epithelial cells to epinephrine*. Br J Pharmacol, 1999. 128(1): p. 227-33.
18. Plesa, M., et al., *The SlyB outer membrane lipoprotein of Burkholderia multivorans contributes to membrane integrity*. Res Microbiol, 2006. 157(6): p. 582-92.
19. Towbin, H., Theophil Staehelin, and Julian Gordon, *Electrophoretic transfer of proteins from polyacrylamide gels to nitrocellulose sheets: Procedure and some applications*. Biochemistry, 1979. 76: p. 4350-4354.
20. Shevchenko, A., et al., *In-gel digestion for mass spectrometric characterization of proteins and proteomes*. Nat. Protocols, 2007. 1(6): p. 2856-2860.
21. Lubitz, W. and von Specht, B. U., *New approaches in vaccine development*, 1999 (*NAVD '99, 15-18 May, 1999, Vienna, Austria*) *and new approaches to bacterial vaccine development* (*NABVD '99, 19-22 May 1999, Munich, Germany*). J Biotechnol, 2000. 83(1-2): p. 1-2.
22. von Specht et al. *Immunogenic efficacy of differently produced recombinant vaccines candidates against Pseudomonas aeruginosainfections*. J Biotechnol, 2000. 83(1-2): p. 3-12.
23. Mansouri et al. *Safety and immunogenicity of a Pseudomonal aeruginosa hybrid outer membrane protein F-I vaccine in human volunteers*. Infect Immun, 1999. 67(3): p. 1461-1470.
24. Garmise R. J. et al., *Formulation of a dry powder influenza vaccine for nasal delivery*. AAPS Pharm Sci Tech, 2006. 7(1): E19.
25. Makidon, P. E., et al., *Induction of immune response to the 17 kDa OMPA Burkholderia cenocepacia polypeptide and protection against pulmonary infection in mice after nasal vaccination with an OMP nanoemulsion-based vaccine*. Med Microbiol Immunol, 2010. 199(2): p. 81-92.
26. Bertot, G. M., et al., *Nasal immunization with Burkholderia multivorans outer membrane proteins and the mucosal adjuvant adamantylamide dipeptide confers efficient protection against experimental lung infections with B. multivorans and B. cenocepacia*. Infect Immun, 2007. 75(6): p. 2740-52.
27. Jiang Q. et al., *A novel recombinant DNA vaccine encoding Mycobacterium tuberculosis ESAT-6 and FL protects against Mycobacterium tuberculosis challenge in mice*. J Biomed Res, 2013. 27(5): 406-420.).
28. Kutzler et al; *Natl Rev Genet*. 2008 October; 9(10):776-88. doi: 10.1038/nrg2432

The invention claimed is:

1. A method of inducing an immune response to protect against or treat a *Burkholderia* infection in an individual, comprising a step of administering to the individual a therapeutically effective amount of an agent comprising a polypeptide of SEQUENCE ID NO:1.

2. The method according to claim 1, wherein the agent further comprises a polypeptide of SEQUENCE ID NO:3.

3. A method of inducing an immune response in an individual with chronic granulomatous disease who does not have an infection caused by a *Burkholderia* strain to protect against a chronic lung infection by *Burkholderia cepacia* complex (Bcc) in said individual, comprising a step of administering to the individual a therapeutically effective amount of an agent selected from: a polypeptide of SEQUENCE ID NO:1; and a polypeptide of SEQUENCE ID NO:3.

4. A method of inducing an immune response to protect against melioidosis caused by a *Burkholderia pseudomallei* infection in an individual, comprising a step of administering to the individual a therapeutically effective amount of an agent consisting of an OMPW protein expressed by *B. pseudomallei* having an approximate molecular weight of 22kDA and an approximate PI of 7.8 to 9 and a GenInfo identifier of GI:134251653.

* * * * *

SEQUENCE LISTING

```
<160> NUMBER OF SEQ ID NOS: 10

<210> SEQ ID NO 1
<211> LENGTH: 271
<212> TYPE: PRT
<213> ORGANISM: Burkholderia multivorans

<400> SEQUENCE: 1

Met Asn Asn Leu His Arg Glu Leu Ala Pro Ile Ser Ser Ala Ala Trp
1               5                   10                  15

Glu Gln Ile Glu Glu Val Ala Arg Thr Phe Lys Arg Ser Val Ala
            20                  25                  30

Gly Arg Arg Val Val Asp Val Glu Gly Pro Lys Gly Pro Glu Leu Ser
        35                  40                  45

Ala Val Gly Thr Gly His Leu Arg Asp Val Ala Ala Pro Arg Glu His
    50                  55                  60

Val Asp Ala Arg Leu Arg Glu Val Arg Thr Ile Val Glu Leu Thr Val
65                  70                  75                  80

Pro Phe Glu Leu Asp Arg Ala Ala Ile Asp Ser Val Glu Arg Gly Ala
                85                  90                  95

Arg Asp Ala Asp Trp Gln Ala Ala Lys Glu Ala Ala Gln Arg Leu Ala
```

-continued

```
            100                 105                 110

Phe Ala Glu Asp Ser Ala Ile Phe Asp Gly Tyr Pro Ala Ala Gly Ile
        115                 120                 125

Val Gly Ile Arg Glu Gly Thr Ser Asn Arg Lys Leu Thr Leu Pro Ser
    130                 135                 140

Asp Val Gly Ala Tyr Pro Asp Ala Ile Ser Asp Ala Leu Glu Ala Leu
145                 150                 155                 160

Arg Leu Ala Gly Val Asp Gly Pro Tyr Ser Val Leu Leu Gly Ala Asp
                165                 170                 175

Ala Tyr Thr Ala Leu Ser Glu Ala Arg Asp Gln Gly Tyr Pro Val Ile
            180                 185                 190

Glu His Ile Lys Arg Ile Val Ser Gly Glu Ile Ile Trp Ala Pro Ala
        195                 200                 205

Ile Ser Gly Gly Cys Val Leu Ser Thr Arg Gly Gly Asp Tyr Glu Leu
    210                 215                 220

His Leu Gly Glu Asp Val Ser Ile Gly Tyr Ala Ser His Thr Asp Lys
225                 230                 235                 240

Val Val Arg Leu Tyr Leu Arg Glu Thr Leu Thr Phe Leu Met Leu Thr
                245                 250                 255

Ser Glu Ala Ser Val Ala Val Ala Pro Ala Ala Gly Thr Pro Ala
            260                 265                 270
```

<210> SEQ ID NO 2
<211> LENGTH: 840
<212> TYPE: DNA
<213> ORGANISM: Burkholderia multivorans

<400> SEQUENCE: 2

```
atgaacaatc tgcaccgcga actcgcgccg atctccagcg ccgcctggga gcaaatcgag      60
gaagaagtcg cgcgcacctt caagcggtcg gtggccggcc gccgcgtggt cgacgtcgag     120
ggcccgaagg gccccgaact ctcggccgtc ggcaccgggc acctgcgcga cgtcgcggcg     180
ccgcgcgagc acgtcgatgc gcggctgcgc gaggtgcgca cgatcgtcga gctgacggtg     240
ccgttcgaac tcgaccgcgc ggcgatcgac agcgtcgagc gcggcgcgcg cgacgccgac     300
tggcaggcgg ccaaggaagc cgcgcagcga ctcgcgttcg cggaagacag cgcgatcttc     360
gacggctatc cggccgccgg catcgtcggg atccgcgaag gcacgtcgaa ccgcaagctc     420
acgctgccga gcgacgtcgg cgcctatccg gacgccatca gcgatgcgct cgaggcgctg     480
cgcctcgcgg gcgtcgacgg cccgtactcg gtgctgctcg gcgccgacgc ctataccgcg     540
ctcagcgagg cacgcgatca gggctatccg gtcatcgagc acatcaagcg gatcgtcagc     600
ggcgagatca tctgggcgcc ggcgatcagc ggcggctgcg tgctgtcgac gcgcggcggc     660
gattacgagc ttcatctcgg cgaagacgtg tcgatcggct atgcgagcca caccgacaag     720
gtcgttcgcc tgtatctgcg cgaaaccttg acgttcctga tgctgacgag cgaagcgtcg     780
gtcgcggtcg cgccggccgc cggcacgccc gcctgatgcg ccgcccgcgc gcgatgccgg     840
```

<210> SEQ ID NO 3
<211> LENGTH: 215
<212> TYPE: PRT
<213> ORGANISM: Burkholderia multivorans

<400> SEQUENCE: 3

```
Met His Gln Thr Asn Asp Thr Ile Arg Thr Arg Ile Ile Ala Ala Ala
1               5                   10                  15
```

Val Val Ala Ala Ser Val Ala Leu Pro Ser Leu Ala Gln Ala Ser
              20                  25                  30

Pro Gly Asp Gly Ile His Gln Gly Asp Val Leu Val Arg Leu Arg Ala
             35                  40                  45

Ile Ser Ile Gln Pro Asn Glu Arg Gly Ser Asp Thr Leu Gly Ala Leu
 50                  55                  60

Asn Val Gly Val Asn Asn Ala Ile Val Pro Glu Leu Asp Phe Thr Tyr
 65                  70                  75                  80

Met Ile Arg Asp Tyr Leu Gly Val Glu Leu Ile Leu Gly Thr Ser Arg
                 85                  90                  95

His Gln Val Thr Ser Ser Ala Gly His Leu Gly Gly Val Asn Val Leu
                100                 105                 110

Pro Pro Thr Leu Leu Leu Gln Tyr His Phe Asn His Ala Gly Lys Val
                115                 120                 125

Arg Pro Tyr Val Gly Ala Gly Leu Asn Tyr Thr Tyr Phe Tyr Asn Asn
            130                 135                 140

Gly Leu Asn Val Gly Gly Glu Gly Val Ser Ile Gly Lys Ser Ser Phe
145                 150                 155                 160

Gly Pro Ala Leu Gln Phe Gly Val Asp Val Gln Met Thr Lys Arg Val
                165                 170                 175

Phe Leu Asn Val Asp Val Lys Lys Ile Trp Met Ser Thr Asp Ala Thr
            180                 185                 190

Leu Gly Asp Arg Gly Ile Gly Thr Leu His Ile Asp Pro Leu Ile Val
            195                 200                 205

Gly Val Gly Val Gly Met Lys
210                 215

<210> SEQ ID NO 4
<211> LENGTH: 651
<212> TYPE: DNA
<213> ORGANISM: Burkholderia multivorans

<400> SEQUENCE: 4
atgcatcaaa ccaatgacac gattcgaaca cgcatcatcg ccgcggccgt ggtggccgcg      60
agcgtcgcgc tgccgtcgct cgcgcaggcg gcgtcgcccg gcgacggcat tcatcagggc     120
gacgtgctcg tgcggctgcg cgcgatcagc atccagccga acgagcgcgg cagcgacacg     180
ctcggcgcgc tgaacgtcgg cgtgaacaac gcgatcgtgc cggagctcga cttcacgtac     240
atgatccgcg actacctggg cgtcgagctg atcctcggca cgtcgcggca tcaggtgacg     300
tcgagcgcgg gccatctcgg cggcgtgaac gtgctgccgc cgacgctgct gctgcagtac     360
cacttcaatc atgcgggcaa ggtgcggccg tacgtcggcg cggggctgaa ctacacgtac     420
ttctacaaca acgggctcaa cgtcggcggc gagggcgtgt cgatcggcaa gagcagcttc     480
gggccggcgc tgcagttcgg cgtggacgtg cagatgacga agcgcgtgtt cctgaacgtc     540
gacgtgaaga agatctggat gagcacggac gcgacgctcg gcgaccgcgg catcggcacg     600
ctgcatatcg atccgctgat cgtcggcgtg ggtgtcggga tgaagttcta g            651

<210> SEQ ID NO 5
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 5

```
caccatgaac aatctgcacc gcgaactc                                    28

<210> SEQ ID NO 6
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 6
atcaggcggg cgtgccggc                                              19

<210> SEQ ID NO 7
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 7
caccatgcat caaaccaatg aca                                         23

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 8
ctagaacttc atcccgacac c                                           21

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
caccatgcat aaaacgattc ga                                          22

<210> SEQ ID NO 10
<211> LENGTH: 21
<212> TYPE: DNA
<213> ORGANISM: Artificial Sequence
<220> FEATURE:
<223> OTHER INFORMATION: Synthetic Olignucleotide

<400> SEQUENCE: 10
ctagaacttc atcccgacgc c                                           21
```